United States Patent [19]
Yamamoto

[11] Patent Number: 5,798,880
[45] Date of Patent: Aug. 25, 1998

[54] REFLECTED LIGHT RECEIVING METHOD

[75] Inventor: Kazushige Yamamoto, Koganei, Japan

[73] Assignee: Tokyo Gas Co., Ltd., Tokyo, Japan

[21] Appl. No.: 716,477

[22] Filed: Sep. 19, 1996

Related U.S. Application Data

[60] Division of Ser. No. 349,878, Dec. 6, 1994, Pat. No. 5,604,643, which is a continuation-in-part of Ser. No. 216,481, Mar. 22, 1994, abandoned.

[51] Int. Cl.$^6$ .............................. G02B 5/10; G02B 17/00
[52] U.S. Cl. ......................... 359/857; 359/858; 359/365
[58] Field of Search ............................ 359/857, 858, 359/861, 862, 863, 865, 356; 356/246, 437

[56] References Cited

U.S. PATENT DOCUMENTS

| | | | |
|---|---|---|---|
| 3,726,598 | 4/1973 | Gilby | 359/365 |
| 3,825,325 | 7/1974 | Hartley et al. | 359/858 |
| 4,209,232 | 6/1980 | Chernin | 359/858 |
| 4,626,078 | 12/1986 | Chernin et al. | 359/858 |
| 4,676,652 | 6/1987 | Chernin | 359/858 |

OTHER PUBLICATIONS

Chernin et al., "Optical Multipass Matrix Systems", *Applied Optics*, Jan. 1, 1991, vol. 30 No. 1 pp. 51–58.

*Primary Examiner*—Thong Nguyen
*Assistant Examiner*—Mohammad Y. Sikder
*Attorney, Agent, or Firm*—Banner & Witcoff Ltd

[57] ABSTRACT

A multiple reflection optical instrument including a housing; a main field mirror fixedly mounted on a mount which is disposed at one longitudinal end of the housing and has a light beam inlet window; an auxiliary field mirror fixedly mounted on the mount which is adjacent to the main field mirror; a light beam outlet window formed in the mount; and first to fourth objective mirrors arranged at the other longitudinal end of the housing opposite to the field mirrors, wherein an image matrix is formed on the main and auxiliary field mirrors by a plurality of reflection spots of the light beam passing through the inlet window into the housing, and a position of a center of curvature of each of the first to fourth objective mirrors, which is projected onto the main field mirror, is adjusted such that the finally reflected light beam toward the outlet window is a maximum even-numbered coming and going reflection reflected from the third objective mirror in the image matrix. The present invention further provides a novel reflected light catching method using the foregoing instrument.

4 Claims, 8 Drawing Sheets

REFLECTED LIGHT RECEIVING METHOD

RELATED APPLICATION

This application is a division of U.S. application Ser. No. 08/349,878 filed Dec. 6, 1994, entitled "Multiple Reflection Optical Instrument and Reflected Light Catching Method Using the Same", U.S. Pat. No. 5,604,643, which is a continuation-in-part of U.S. application Ser. No. 08/216,481 filed Mar. 22, 1994, abandoned on Dec. 8, 1994.

BACKGROUND OF THE INVENTION

1. Field of the Invention

The present invention relates to a multiple path optical matrix system and, more particularly, to a multiple reflection optical instrument used for the component analysis of a gas or the like and a reflected light catching method using the same.

2. Description of the Prior Art

In a conventional technique of this type, a laser beam is caused to pass through the housing of a cell in which a gas to be analyzed is charged and the wavelength intensity of the exit light beam is analyzed, thereby performing the component analysis of the gas. In order to perform this analysis, it is necessary to realize an optical path (a transmission path) as long as possible in the housing.

In a classic system developed by White, a plurality of mirrors are used to prolong the optical path. However, this system cannot provide a sufficiently long optical path.

A technique is recently disclosed in U.S. Pat. No. 4,626,078 to Chernin et al. This technique relates to a multiple path optical matrix system having an arrangement schematically shown in FIG. 1 and an operation described below with reference to FIG. 2.

Referring to FIG. 1, this system is constituted by a cylindrical cell having a housing 4. A main field mirror 24 and an auxiliary field mirror 25 adjacent to the main field mirror 24 are arranged at one longitudinal end of the housing 4. On the other hand, a set of four pieces of objective mirrors 39, 40, 41, and 42 having the same radius of curvature are arranged on a mount 34 disposed at the other longitudinal end of the housing 4 opposite to the field mirrors 24 and 25. The main field mirror 24 has the same curvature as that of the objective mirrors. The center of curvature of the main field mirror 24 matches the center of symmetry of the four pieces of objective mirrors along the longitudinal axis of the housing 4. In the multiple reflection optical apparatus having the above arrangement, a light beam from a light source is incident in the housing 4 through an inlet window 2 provided on the field mirrors side. The light beam is repeatedly reflected between one of the objective mirrors 39 to 42 and one of the field mirrors 24 and 25 a plurality of times. The light beam beam finally emerges through an outlet window 27 formed on the side of the inlet window 2, and the wavelength intensity of the light beam emerging from the outlet window 27 is measured. The reflection operation in the housing 4 of the above multiple reflection system will be described below in relation to an image matrix shown in FIG. 2.

The light beam emitted from the light source passes through the inlet window 2 formed at one longitudinal end of the housing 4 formed in the cell. The light beam is directed to the first objective mirror 39 of the four pieces of objective mirrors and reflected thereby toward the main field mirror 24 to perform the first coming and going reflection in the housing 4. A first spot 1 is located at one corner of the image matrix focused on the main field mirror 24. The light beam is directed from the first spot 1 on the main field mirror 24 to the second objective mirror 40, reflected thereby, and directed to the first objective mirror 39 once more through the main field mirror 24. The reflection between the first objective mirror 39 and the field mirror 24 and the reflection between the second objective mirror 40 and the field mirror 24 are alternately repeated a plurality of times until the reflected light beam reaches a seventh spot 7 focused at a cross poit of one end column of the image matrix on the main field mirror 24 which includes the first spot 1 and the lowermost line thereof. At this time, the light beam is incident through the first objective mirror 39 on the auxiliary field mirror 25 provided adjacent to the main field mirror 24 on the inlet window 2 side and having the same curvature as in the objective mirrors and the center of curvature matching the point of symmetry of the first and third objective mirrors 39 and 41. The light beam reflected by the auxiliary field mirror 25 is directed to the third objective mirror 41, incident on the main field mirror 24 again through the third objective mirror 41, and directed to the last fourth objective mirror 42.

After repeating this reflection a plurality of times, the light beam is finally reflected by the first objective mirror 39 in the housing 4, emerges from the housing 4 through the outlet window 27 including a spot corresponding to an odd-numbered coming and going reflection (45th coming and going reflection in FIG. 2) in the housing 4, and is catched by a sensor or the like.

Practically, however, when the above conventional system is used in an environment, e.g., in a running car or flying airplane, which produces a very strong vibration, the cell of the multiple reflection optical instrument is distorted to cause variation of the optical path. This makes it impossible to stably catch the transmitted light beam at the outlet window. This phenomenon will be described below in relation to FIG. 3.

Assume that, during use of the conventional system, distortion of the cell by the vibration causes one mirror M of the field mirrors or the objective mirrors to tilt by an angle $\Delta\alpha$. At this time, a light beam 1 directed to the mirror M makes a light beam 1b reflected from the mirror M, which is shifted by an angle $2\Delta\alpha$ with respect to a reflected light beam 1a in a normal state. That is, the reflected light beam 1b is shifted by an angle twice the tilting angle of the mirror by distortion of the cell. Therefore, the light beam finally reflected in the housing can be greatly shifted from the outlet window depending on the magnitude of distortion of the cell and the length of the housing to make it impossible to catch the light beam. It can be considered to anticipate the maximum distortion of the cell and form an outlet window having an opening area large enough to cope with this shift. However, the size of the cell itself is limited. In addition, when an optical sensor is used in accordance with such a large opening area, the accuracy of the sensor is greatly degraded, and the object to perform the gas analysis or the like cannot be achieved.

Further, when air is sampled in a flying airplane while moving at a high speed, it is difficult to repeat measuring in a specific spot. Therefore, the light beam must be caught without any error.

SUMMARY OF THE INVENTION

The present invention has been made in view of the above situation, and has as its object to provide a multiple reflection optical instrument capable of stably catching the light beam without any shift of the finally reflected light beam from a preset position even when the cell of the multiple reflection optical instrument, in which a gas to be measured is inserted, is distorted by a vibration, and a reflected light catching method using this apparatus.

In order to achieve the above object, according to a first aspect of the present invention, there is provided a multiple reflection optical instrument used for a gas analysis or the like, including (a) a housing formed in a cell, (b) a main field mirror fixedly mounted on a mount which is disposed at one longitudinal end of the housing and is provided with a light beam inlet window for introducing a light beam from a light source into an inside of the housing and with an outlet window for causing a light beam multiple-reflected in the housing to be directed to a measuring equipment, (c) an auxiliary field mirror having the same radius of curvature as that of the main field mirror, fixedly mounted on the mount so as to be adjacent to the main field mirror on the light beam inlet window side, and (d) first to fourth objective mirrors arranged at the other longitudinal end of the housing where is opposite to the two field mirrors and being freely rotated entirely through a holder and also individually in every directions, having equal radii of curvature each equal to that of the main field mirror, and arranged such that a center of curvature of the auxiliary field mirror becomes a point of symmetry between the first and third objective mirrors, wherein an image matrix is formed on the main and auxiliary field mirrors by a plurality of reflection spots of the light beam passing through the inlet window into the housing, and a position of a center of curvature of each of the first to fourth objective mirrors, which is projected onto the main field mirror, is adjusted such that the finally reflected light beam toward the outlet window is a maximum even-numbered coming and going reflection reflected from the third objective mirror in the image matrix.

According to a second aspect of the present invention, there is provided a multiple reflection optical instrument wherein the position of the center of curvature of each of the four pieces of objective mirrors, which is projected onto the main field mirror, is adjusted such that a number of lines of spots arranged in a horizontal direction of the image matrix recited in the first aspect are an odd number.

According to a third aspect of the present invention, there is provided a multiple reflection optical instrument wherein the outlet window recited in either one of the first and second aspects is formed on the auxiliary field mirror.

According to a fourth aspect of the present invention, there is provided a multiple reflection optical instrument wherein the outlet window recited in either one of the first and second aspects is formed on a corner portion of the mount on the side of the auxiliary field mirror where is lower than a lower edge of the auxiliary field mirror.

According to a fifth aspect of the present invention, there is provided a multiple reflection optical instrument wherein the first to fourth objective mirrors recited in the third aspect are adapted such that a center of curvature of the first objective mirror is a point of symmetry between a position of the inlet light beam at the inlet window and a first spot focused through the first objective mirror at a cross point of a left end column of the image matrix on the main field mirror and a lowermost line thereof, that a center of curvature of the second objective mirror is a point of symmetry between the first spot and a second spot focused through the second objective mirror at a cross point of a right end column of the image matrix on the main field mirror and an uppermost line thereof, that a center of curvature of the third objective mirror is a point of symmetry between a spot in a lowermost line on the auxiliary field mirror and a spot focused through the third objective mirror at a cross point of a left end column of the image matrix on the main filed mirror and a second line from the top thereof, that a center of curvature of the fourth objective mirror is a point of symmetry between the spot focused through the third objective mirror at the left end column of the image matrix on the main field mirror and the second line from the top thereof and a spot focused through the fourth objective mirror at a cross point of the right end column of the image matrix on the main field mirror and the lowermost line thereof, that a distance between the centers of curvature of the first and third objective mirrors or between the centers of curvature of the second and fourth objective mirrors is a half of a distance between two spots vertically adjacent to each other, and that a distance between the centers of curvature of the first and second objective mirrors or between the centers of curvature of the third and fourth objective mirrors is a half of a distance between two spots horizontally adjacent to each other.

According to a sixth aspect of the present invention, there is provided a multiple reflection optical instrument wherein the first to fourth objective mirrors recited in the fourth aspect are adapted such that a center of curvature of the first objective mirror is a point of symmetry between a position of the inlet light beam at the inlet window and a first spot focused through the first objective mirror at a cross point of a left end column of the image matrix on the main field mirror and a second line from the bottom thereof, that a center of curvature of the second objective mirror is a point of symmetry between the first spot and a second spot focused through the second objective mirror at a cross point of a right end column of the image matrix on the main field mirror and an uppermost line thereof, that a center of curvature of the third objective mirror is a point of symmetry between a spot in a lowermost line on the auxiliary field mirror and a spot focused through the third objective mirror at a cross point of the left end column of the image matrix on the main field mirror and a third line from the top thereof, that a center of curvature of the fourth objective mirror is a point of symmetry between the spot focused through the third objective mirror at the cross point of the left end column of the image matrix on the main field mirror and the third line from the top thereof and a spot focused through the fourth objective mirror at a cross point of the right end column of the image matrix on the main field mirror and the second line from the bottom thereof, that a distance between the centers of curvature of the first and third objective mirrors or between the centers of curvature of the second and fourth objective mirrors is the same as a distance between two spots vertically adjacent to each other, and that a distance between the centers of curvature of the first and second objective mirrors or between the centers of curvature of the third and fourth objective mirrors is a half of a distance between two spots horizontally adjacent to each other.

Further, according to the seventh aspect of the present invention, there is provided a reflected light catching method in a multiple path optical matrix system, including:

causing a light beam from a light source to pass through an inlet window formed at a corner portion of one longitudinal end of a housing provided in a cell and causing the light beam to be incident on a first objective mirror of four pieces of objective mirrors having equal radii of curvature to one another and mechanically mounted on a holder arranged at the other longitudinal end of the housing to be freely rotated about vertical and horizontal axes with respect to an image matrix, reflecting the light beam by the first objective mirror and causing the light beam to be incident on a first spot of a lowermost line in a column on one end side of the image matrix formed on a main field mirror having the same radius of curvature as that of the objective mirrors and arranged on one longitudinal end of the housing such that a center of curvature matches a center of symmetry of the four pieces of objective mirrors along a longitudinal axis of the housing, directing the light beam reflected from the first spot on the main field mirror to a second objective mirror placed at a diagonal position with respect to the first objective mirror, directing the light beam reflected from the second objective mirror to the main field mirror, then reflecting the light beam thereby to the first objective mirror, alternately repeating a reflection between the first objective mirror and the main field mirror and a reflection between the second objective mirror and the main field mirror a plurality of times, and causing the light beam to reach the column vertically focused on one end side of the image matrix which includes the first spot, causing the reflected light beam present on the spot at one end side to be incident, through the first objective mirror, on an auxiliary field mirror arranged adjacent to the main field mirror on the inlet window side, and having the same curvature as that of each of the objective mirrors and a center of curvature matching a point of symmetry between the first and third objective mirrors, subsequently reflecting the light beam by the auxiliary field mirror to the third objective mirror arranged at a position parallel to the second objective mirror and perpendicular to the first objective mirror, causing the light beam reflected by the third objective mirror to be incident on the main field mirror again and then reflecting the light beam thereby to a fourth objective mirror placed at a diagonal position with respect to the third objective mirror, directing the light beam reflected by the fourth objective mirror to the main field mirror, then reflecting the light beam thereby to the third objective mirror, and alternately repeating a reflection between the third objective mirror and the main field mirror and a reflection between the fourth objective mirror and the main field mirror a plurality of times, alternately repeating the reflections between the first and second objective mirrors and the main field mirror a plurality of times again, alternately repeating the reflections between the third and fourth objective mirrors and the main field mirror a plurality of times again, and causing the light beam finally passing through the housing to emerge from the housing through an outlet window formed on one longitudinal side of and one end of the housing, wherein the finally passing light beam is a reflected light beam toward a spot corresponding to a maximum even-numbered coming and going reflection in the image matrix, the reflected light beam toward the spot corresponding to the even-numbered coming and going reflection is a light beam finally reflected through the third objective mirror, and the finally reflected light beam is caused to emerge from the housing through the outlet window formed at a cross point of the other side end column of the image matrix including spots focused on the auxiliary field mirror and the center line thereof.

Still further, according to the eighth aspect of the present invention, there is provided a reflected light catching method in a multiple path optical matrix system, including:

causing a light beam from a light source to pass through an inlet window formed at a corner portion of a mount arranged at one longitudinal end of a housing provided in a cell and causing the light beam to be incident on a first objective mirror of four pieces of objective mirrors having equal radii of curvature to one another and mechanically mounted on a holder arranged at the other longitudinal end of the housing to be freely rotated about vertical and horizontal axes with respect to an image matrix, reflecting the light beam by the first objective mirror and causing the light beam to be incident on a first spot of the image matrix formed on a main field mirror having the same radius of curvature as that of each of the objective mirrors and arranged on one longitudinal end of the housing such that a center of curvature matches a center of symmetry of the four pieces of objective mirrors along a longitudinal axis of the housing, directing the light beam reflected from the first spot on the main field mirror to a second objective mirror placed at a diagonal position with respect to the first objective mirror, directing the light beam reflected from the second objective mirror to the main field mirror, then reflecting the light beam thereby to the first objective mirror, alternately repeating a reflection between the first objective mirror and the main field mirror and a reflection between the second objective mirror and the main field mirror a plurality of times, and causing the light beam to reach the column vertically focused on one end side of the image matrix which includes the first spot, causing the reflected light beam present on the spot at one end side to be incident, through the first objective mirror, an auxiliary field mirror arranged adjacent to the main field mirror on the inlet window side, and having the same curvature as that of each of the objective mirrors and a center of curvature matching a point of symmetry between the first and third objective mirrors, subsequently reflecting the light beam by the auxiliary field mirror to the third objective mirror arranged at a position parallel to the second objective mirror and perpendicular to the first objective mirror, causing the light beam reflected by the third objective mirror to be incident on the main field mirror again and then reflecting the light beam thereby to a fourth objective mirror placed at a diagonal position with respect to the third objective mirror, directing the light beam reflected by the fourth objective mirror to the main field mirror, then reflecting the light beam thereby to the third objective mirror, and alternately repeating a reflection between the third objective mirror and the main field mirror and a reflection between the fourth objective mirror and the main field mirror a plurality of times, alternately repeating the reflections between the first and second objective mirrors and the main field mirror a plurality of times again, alternately repeating the reflections between the third and fourth objective mirrors and the main field mirror a plurality of times again, and causing the light beam finally passing through the housing to emerge from the housing through an outlet window formed on one longitudinal side of and one end of the housing, wherein the first spot is focused at a cross point of one end column of the image matrix on the main field mirror where is spaced most apart from the auxiliary field mirror and a second line from the bottom thereof and, on the other hand, the finally passing light beam is a reflected light beam directed to a spot corresponding to a maximum even-numbered coming and going reflection in the image matrix, the reflected light beam toward the spot corresponding to the even-numbered coming and going reflection is a light beam finally reflected through the third objective mirror, and the reflected light beam is caused to emerge from the housing through the outlet window formed at a cross point of the other side end column of the image matrix including spots focused on the auxiliary field mirror and in the lowermost line thereof.

According to the ninth aspect of the present invention, there is provided a reflected light catching method, including adjusting the position of the center of curvature of each of the four objective mirrors, which is projected onto the mainfield mirror, such that a number of lines of spots arranged in a horizontal direction of the image matrix are an odd number.

According to the tenth aspect of the present invention, there is provided a reflected light catching method, including adjusting the position of the center of curvature of each of the four objective mirrors, which is projected onto the main field mirror, such that a number of lines of spots arranged in a horizontal direction of the image matrix are an odd number.

As described above, according to the present invention having the above aspects, the light beam is reflected between the objective mirrors and the opposing field mirrors even-numbered times at maximum. With this operation, the shift of the reflected light beam at the outlet window can be prevented, and an optical path having a sufficient length can be ensured in a gas detection housing. For this reason, even in an environment, e.g., in a running car or flying airplane, which produces a strong vibration, the reflected light beam can be certainly caught. Therefore, a stable gas analysis can be effectively performed.

The above and other objects, aspects, and advantages of the present invention will be apparent to one skilled in the art from the explanation in relation to the following description and the accompanying drawings, in which the preferred detailed examples according with the principle of the present invention are illustrated as embodiments.

DETAILED DESCRIPTION OF THE PREFERRED EMBODIMENTS

The present invention will be described below in more detail in relation to some preferred embodiments shown in the accompanying drawings (FIGS. 4 to 11).

Figure 1:
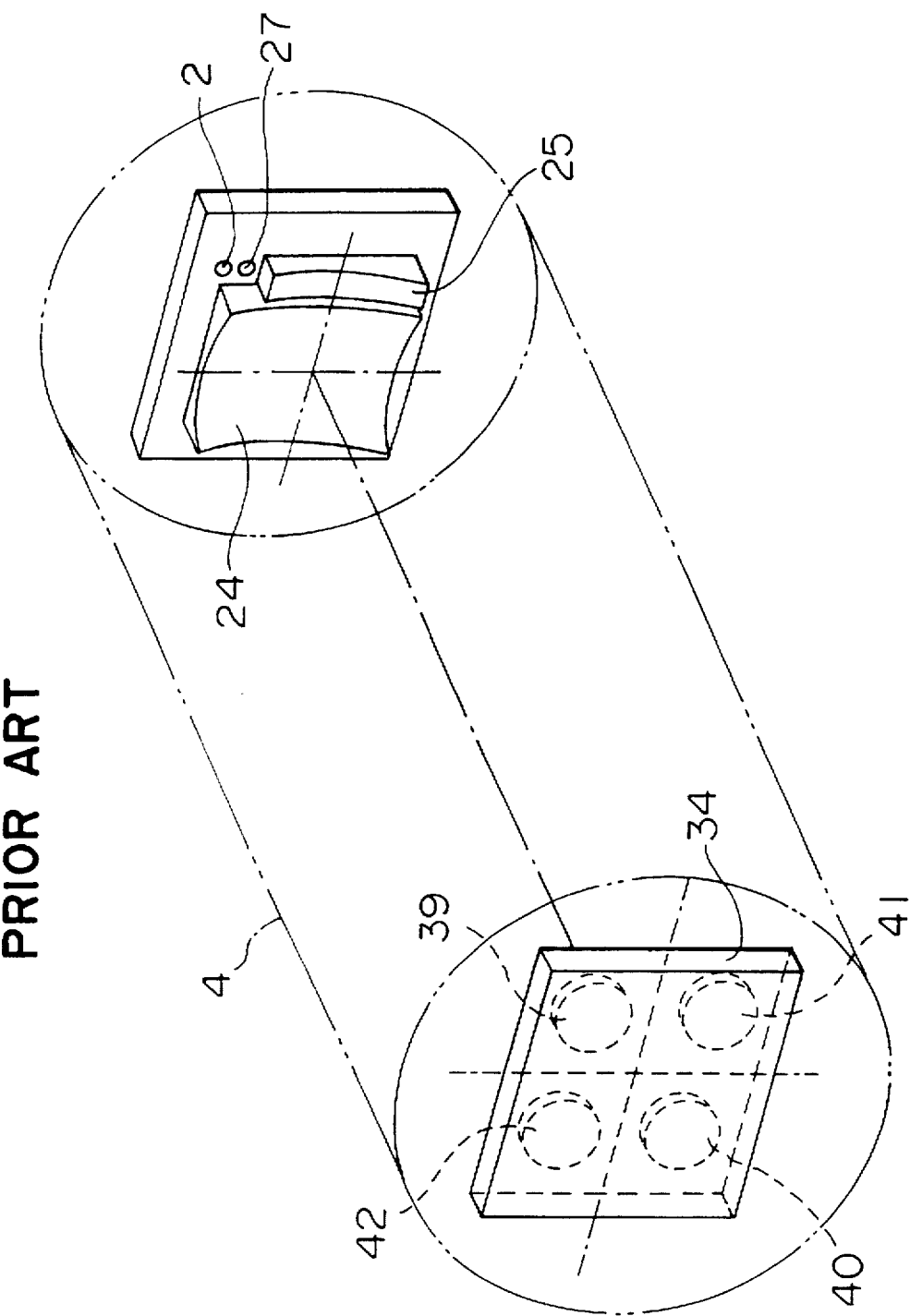
FIG. 1 is a schematic perspective view showing a conventional multiple reflection optical instrument.
Figure 2:
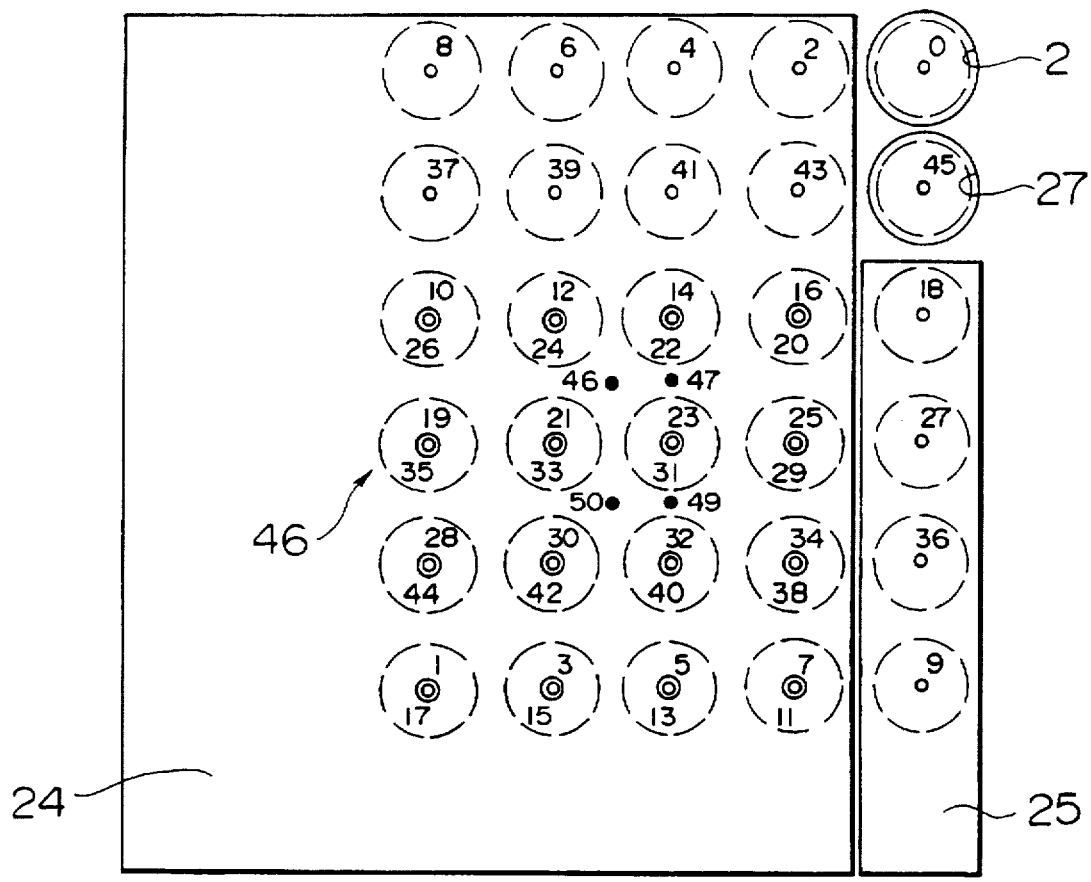
FIG. 2 is an image matrix by a conventional reflected light catching method.
Figure 3:
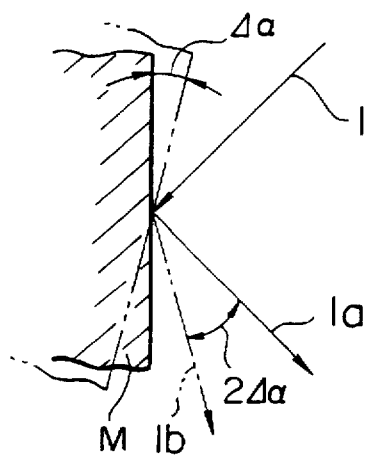
FIG. 3 is an explanatory view related to the shift of a reflected light beam in the multiple reflection optical instrument.
Figure 4:
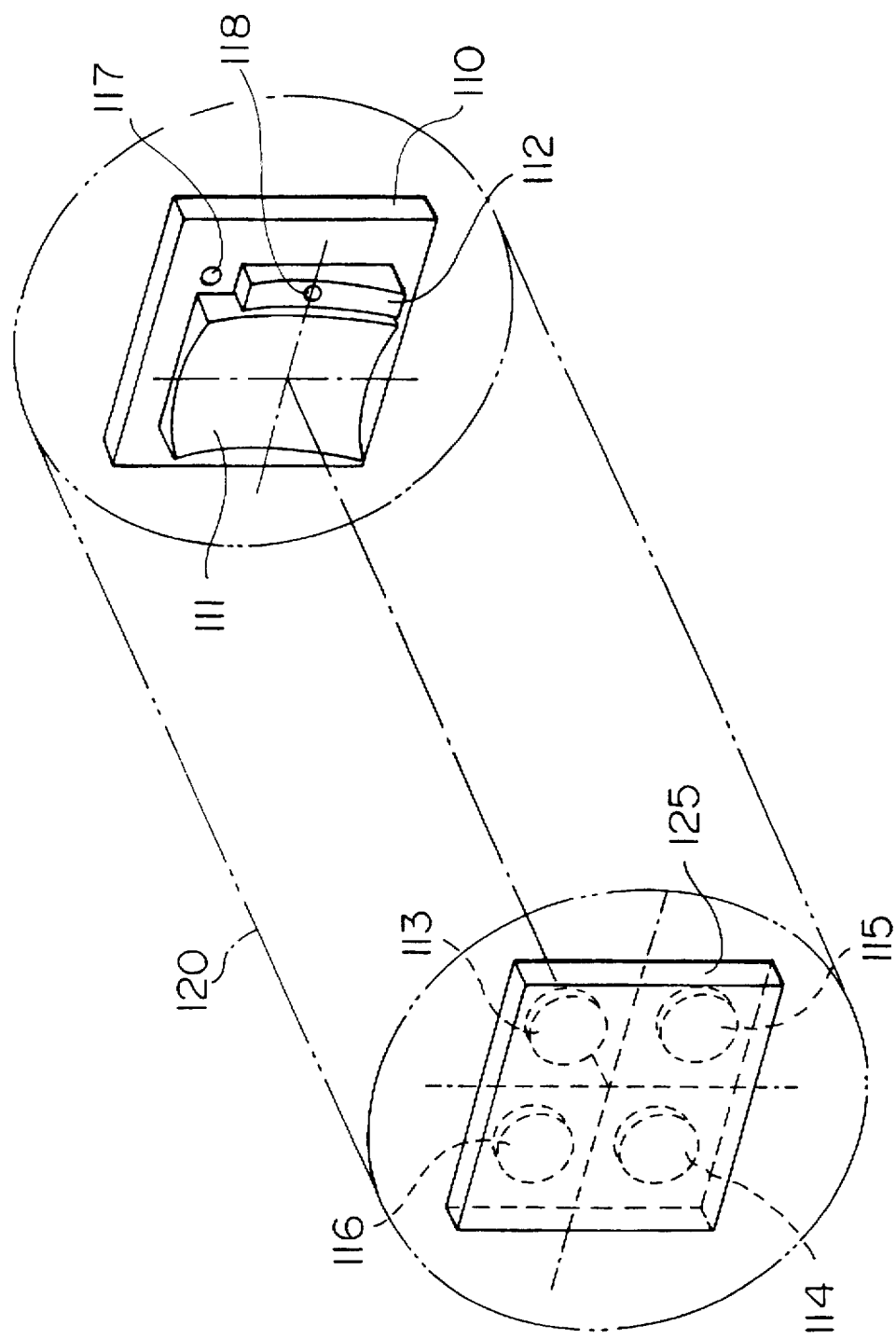
FIG. 4 is a schematic perspective view showing a first embodiment of a multiple reflection optical instrument of the present invention.

FIG. 4 is a schematic perspective view showing a first embodiment of a multiple reflection optical instrument of the present invention. This instrument has almost the same arrangement as in the conventional instrument shown in FIG. 1 except for the position where an outlet opening (outlet window) of the reflected light beam is formed and the position of the center of curvature of each objective mirror on a main field mirror. Therefore, a detailed description of the instrument will be omitted so as to avoid repetition.

A main field mirror 111 is fixedly mounted on a mount 110, at one end of a housing 120 provided in a cell of the instrument. An auxiliary field mirror 112 is fixedly mounted on the mount 110 so as to be adjacent to one side of the main field mirror 111 and has the same curvature as that of the main field mirror 111.

Four pieces of objective mirrors 113, 114, 115 and 116 are identical to each other and have the same curvature as that of the main and the auxiliary field mirrors 111 and 112. These objective mirrors are arranged, through a holder 125, at the other longitudinal end of the housing 120, where is opposite to the field mirrors 111 and 112, and are movable together and also individually in every directions. An outlet window 118 is formed in the auxiliary field mirror 112.

Figure 5:
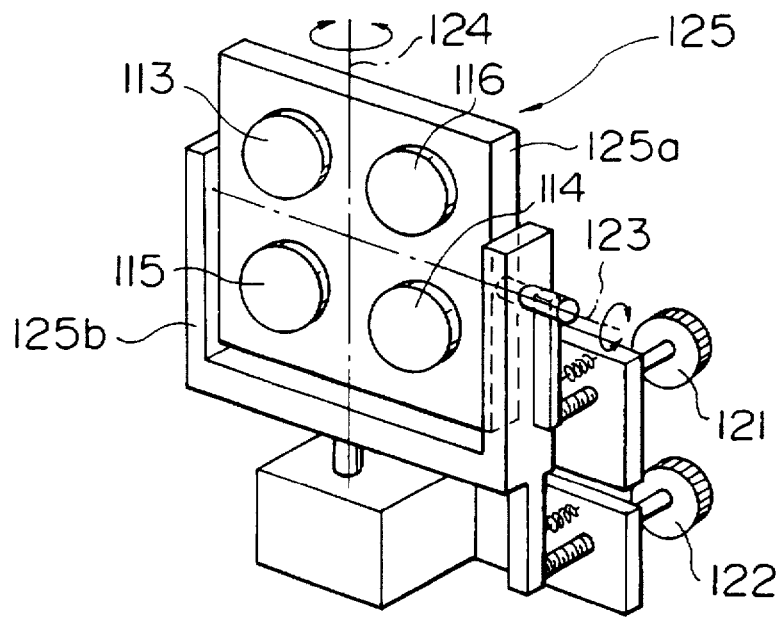
FIG. 5 is a schematic perspective view showing a holder on which four objective mirrors are mechanically mounted to be adjustable in angles.

The holder 125 for mechanically mounting the objective mirrors 113, 114, 115 and 116 will be described below in detail with reference to FIG. 5.

The holder 125 includes a first mount 125a having the four objective mirrors 113, 114, 115, and 116 arranged to be movable and a second mount 125b for rotating the first mount 125a about a central vertical axis 124. The first mount 125a is rotated about a central horizontal axis 123 by an adjusting knob 121 and rotated by another adjusting knob 122 about the vertical axis 124 through the second mount 125b. The angular position of each of the objective mirrors 113, 114, 115 and 116 can be adjusted by an adjusting knob (not shown). Adjustment by these adjusting knobs 121, 122 determines the direction of a light beam reflected to the field mirror 111 and the auxiliary field mirror 112.

When the adjusting knob 122 is fixed and the adjusting knob 121 is adjusted, the four pieces of objective mirrors are rotated about the horizontal axis 123.

When the adjusting knob 121 is fixed and the adjusting knob 122 is adjusted, the four pieces of objective mirrors are rotated about the vertical axis 124.

The center of curvature of the auxiliary field mirror 112 is located at the point of symmetry of the first and third objective mirrors 113 and 115.

When the reflection angles of the objective mirrors 113, 114, 115 and 116 are respectively adjusted by the adjusting knobs (none are shown), the number of lines and columns of an image matrix formed on the field mirrors 111 and 112 is determined.

When the four pieces of objective mirrors are rotated about the horizontal axis 123, the reflection angle of the light beam to the field mirrors 111 and 112 along the horizontal direction is changed. The number of lines of the image matrix along the horizontal direction is thus increased or decreased. On the other hand, when the four pieces of objective mirrors are rotated about the vertical axis 124, the reflection angle of the light beam to the field mirrors 111 and 112 along the vertical direction is changed. Therefore, the number of columns of the image matrix along the vertical direction is increased or decreased.

Figure 6:
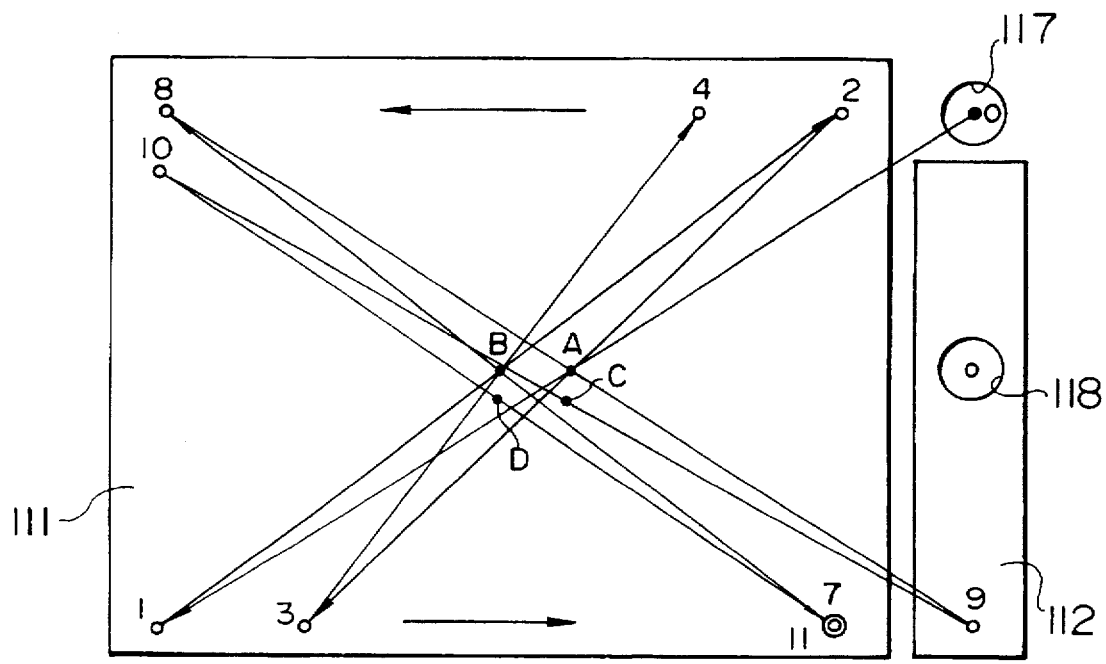
FIG. 6 is a view showing an image matrix representing the spots of a light beam focused on a main field mirror and an auxiliary field mirror.

FIG. 6 is a view showing an image matrix representing the spots of the light beam focused on the main field mirror 111 and the auxiliary field mirror 112. The reflection operation of the light beam in the first embodiment will be described with reference to FIG. 6.

(1) Reference numeral 0 denotes an incident position of the light beam passing through an inlet window 117. The light beam is reflected through the first objective mirror 113 and directed to a first spot 1 of the image matrix focused on the main field mirror 111. The first spot 1 is positioned at a cross point of one end column of the image matrix, where is spaced most apart from the auxiliary field mirror 112, and the lowermost line thereof.

(2) The light beam is reflected from the first spot 1 focused on the main field mirror 111, and then directed to the second objective mirror 114. The light beam is further reflected by the objective mirror 114, and directed to a second spot 2 on the main field mirror 111. The second spot 2 is focused at a cross point of the other end column of the image matrix, where is in the most vicinity of the auxiliary field mirror 112, and the uppermost line thereof.

(3) The light beam reflected by the second spot 2 is directed through the first objective mirror 113 to a third spot 3 on the main field mirror 111 which is adjacent to the first spot 1 in the horizontal direction.

(4) The light beam reflected by the third spot 3 is directed through the second objective mirror 114 to a fourth spot on the main field mirror 111 which is adjacent to the second spot 2 in the horizontal direction.

(5) The light beam reflected by the fourth spot 4 is directed through the first objective mirror 113 again to the next spot. Such reflections between the first objective mirror 113 and the main field mirror 111 and between the second objective mirror 114 and the main field mirror 111 are alternately repeated a plurality of times until the light beam is incident on a spot 7 formed at a cross point of the right end column of the image matrix on the main field mirror 111 and the lowermost line thereof. The light beam is then reflected through the second objective mirror 114 to a spot 8 formed at a cross point of the left end column of the image matrix and the uppermost line thereof.

(6) The light beam reflected by the spot 8 is directed through the first objective mirror 113 to a spot 9 formed in the lowermost line on the auxiliary field mirror 112.

(7) The light beam reflected from the spot 9 is incident to the third objective mirror 115 and directed to a spot 10 on the main field mirror 111.

(8) The light beam reflected from the spot 10 is incident to the fourth objective mirror 116 and reflected therethrough to a spot 11 formed at a cross point of the right end column of the image matrix on the main field mirror 111 and the lowermost line thereof. This spot 11 is equal to the spot 7 of the fourth preceding coming and going reflection and these two spots are superposed. This superposition of spots also occurs in other spots except in the uppermost line of the image matrix, in the line including the exit window and in spots formed on the auxiliary field mirror 112. Such a reflection between the third objective mirror 115 and the main field mirror 111 and a reflection between the fourth objective mirror 116 and the main field mirror 111 are alternately repeated a plurality of times. Then again, the reflections between the first and second objective mirrors 113 and 114 and the main field mirror 111 are alternately repeated a plurality of times. Thereafter, the reflections between the third and fourth objective mirrors 115 and 116 and the main field mirror 111 are alternately repeated a plurality of times. With this operation, the spot is moved near the center line of the image matrix formed on the main and auxiliary field mirrors 111 and 112 while increasing the number of spots.

(9) Finally, the light beam is reflected through the third objective mirror 115 and caused to emerge through the outlet window 118 (FIG. 4) including the spot of the reflected light beam corresponding to an even-numbered coming and going reflection.

In the reflected light catching method of the present invention, the finally reflected light beam is caused to emerge through the outlet window 118 including the spot of the reflected light beam corresponding to an even-numbered coming and going reflection. The reason for this is as follows. When the relative position of the incident light beam and the field mirrors 111 and 112 and the relative position of the centers of curvature of the objective mirrors 113 to 116 projected onto the main field mirror 111 are not changed by a vibration or the like, the spot of the reflected light beam on the field mirror corresponding to an even-numbered coming and going reflection is not shifted although the spot of the reflected light beam on the field mirror corresponding to an odd-numbered coming and going reflection is shifted. The reason for this will be described with reference to FIG. 8.

Figure 8:
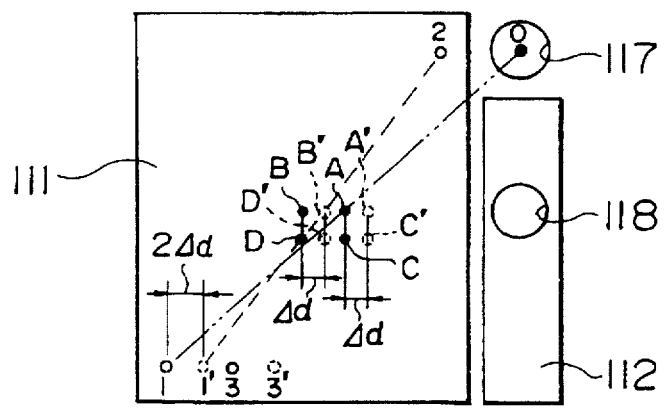
FIG. 8 is an explanatory view showing the relationship between the shift of the centers of curvature of objective mirrors and the shift of spots on the main field mirror.

Referring to FIG. 8, the light beam passing through the inlet window 117 is reflected by the first objective mirror 113 (not shown) and forms the spot 1 (odd-numbered) on the main field mirror 111. For example, if the apparatus is distorted by a vibration in a horizontal direction, and the position of a center A of curvature of the objective mirror 113 projected onto the main field mirror 111 is shifted by $\Delta\alpha$ to the right to become a position A'. At this time, the position of the spot 1 focused on the main field mirror 111 is shifted by $2\Delta$ to the right to become a spot 1'. Subsequently, the light beam from the spot 1' shifted by $2\Delta\alpha$ is reflected by the second objective mirror 114 (not shown) which projects a center B of curvature onto the main field mirror 111 to form the spot 2 (even-numbered) on the main field mirror 111 again. Since the center B of curvature is also shifted by $\Delta\alpha$ in advance, the shift is offset. Thus, the position of the spot 2 is not shifted regardless of the distortion of the apparatus by a vibration. In the subsequent reflections, the odd-numbered and even-numbered coming and going reflections are alternately repeated. This can also be applied when reflections by the third and fourth objective mirrors are started.

In the first embodiment of the multiple reflection optical instrument of the present invention, the arrangement of columns and lines of the image matrix shown in FIG. 6 is determined such that the following conditions are satisfied.

(a) The point A of symmetry between the position 0 of the inlet light beam at the inlet window 117 and the first spot 1 focused on the main field mirror 111 through the first objective mirror 113 at a cross point of a left end column of the image matrix and the lowermost line thereof becomes the center of curvature of the first objective mirror 113.

(b) The point B of symmetry between the first spot 1 and the second spot 2 focused through the second objective mirror 114 at a cross point of the right end column of the image matrix on the main field mirror 111 and the uppermost line thereof becomes the center of curvature of the second objective mirror 114.

(c) A point C of symmetry between the spot 9 in the lowermost line on the auxiliary field mirror 112 and the spot 10 focused on the main field mirror 111 through the third objective mirror 115 at a cross point of the left end column of the image matrix and the second line from the top thereof becomes the center of curvature of the third objective mirror 115.

(d) A point D of symmetry between the spot 10 and the spot 11 focused through the fourth objective mirror 116 at a cross point of the right end column of the image matrix on the main field mirror 111 and the lowermost line thereof becomes the center of curvature of the fourth objective mirror 116.

However, since the size of the housing 120 formed in the multiple reflection optical apparatus is limited in advance, the maximum size of the image matrix formed on the field mirrors 111 and 112 arranged in the housing 120 is apparently limited accordingly. With this limit, in order to cause the reflected light beam from a spot corresponding to an even-numbered coming and going reflection to emerge from the housing 120 and, at the same time, realize an optical path as long as possible for the purpose of stable catching of the reflected light beam, the intervals of spots must be set larger than the diameter of the light beam on the main field mirror including an aberration. In addition, the centers A, B, C and D of curvature of the four objective mirrors, which are projected onto the main field mirrors 111, must be determined such that the number of columns of spots in the image matrix is a maximum natural number of two or more which can be set in the field mirrors 111 and 112, and the number of lines of spots is a maximum odd number of three or more which can be set in the field mirrors 111 and 112. The reason for this will be described below on the basis of FIGS. 9A and 9B.

Figure 9A:
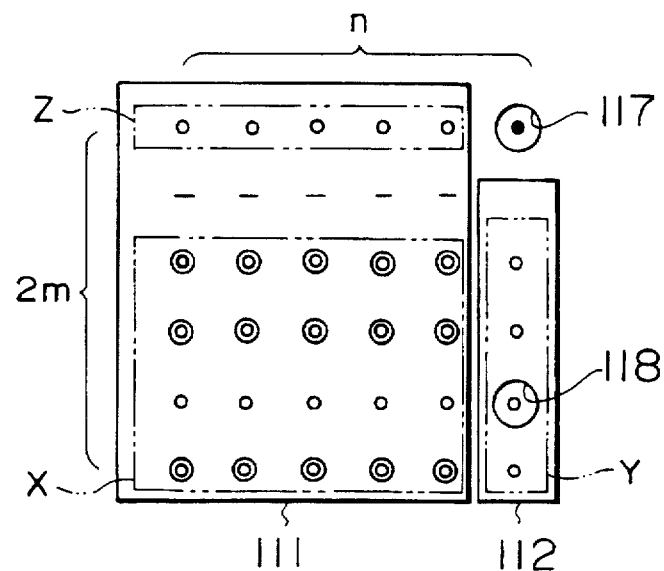
FIGS. 9A and 9B are explanatory views showing an image matrix having an even number of lines when an exit window is set at the position of a spot corresponding to a maximum even-numbered coming and going reflection and an image matrix having an odd number of lines are one line less than the even number of lines, respectively.

FIG. 9A shows an image matrix when the number of columns of spots focused on the field mirrors 111 and 112 are represented by n, the number of lines of spots are an even number represented by 2m, and the outlet window 118 of the light beam is a spot of a maximum even number. As is apparent from this example, when the number of lines are an even number, no spot is focused in the second line from the top. In the uppermost line and the second line from the bottom, the light beam is reflected only once. The number of spots in this example are calculated as follows.

$$\begin{aligned} \{2 \times (2m-2) \times (n-1) - (n-1)\} & \quad \text{(number in area } X\text{)} \\ + (2m-2) & \quad \text{(number in area } Y\text{)} \\ + (n-1) & \quad \text{(number in area } Z\text{)} \\ \hline = (2m-2) \times (2n-1) & \end{aligned} \quad (1)$$

Figure 9B:
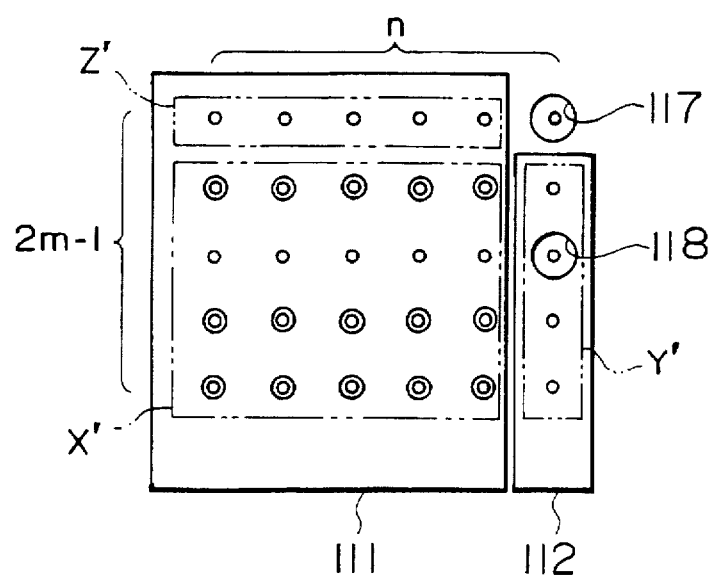

FIG. 9B shows an image matrix when the number of lines of spots are an odd number (2m−1) which are one line smaller than the even number in FIG. 9A, and the finally reflected light beam gotten out from the outlet window 118 is a spot of a maximum even number. As is apparent from this example, when the number of lines are an odd number, in the uppermost and central lines, the light beam is reflected only once. The number of spots in this case are calculated in accordance with the following equation.

$$\begin{aligned} \{2 \times (2m-2) \times (n-1) - (n-1)\} & \quad \text{(number in area } X\text{)} \\ + (2m-2) & \quad \text{(number in area } Y\text{)} \\ + (n-1) & \quad \text{(number in area } Z\text{)} \\ \hline = (2m-2) \times (2n-1) & \end{aligned} \quad (2)$$

As is apparent from the above equations (1) and (2), when the light beam reflected from a spot of a maximum even number is caught, the number of spots of the image matrix having an even number of lines are the same as that in the matrix having an odd number of lines, which are one line smaller than the even number. Therefore, when the matrix having an odd number of lines shown in FIG. 9B is used, the field mirrors can be effectively used rather than use of the matrix having an even number of lines shown in FIG. 9A because the second column from the top is of no use in the latter case.

Figure 7:
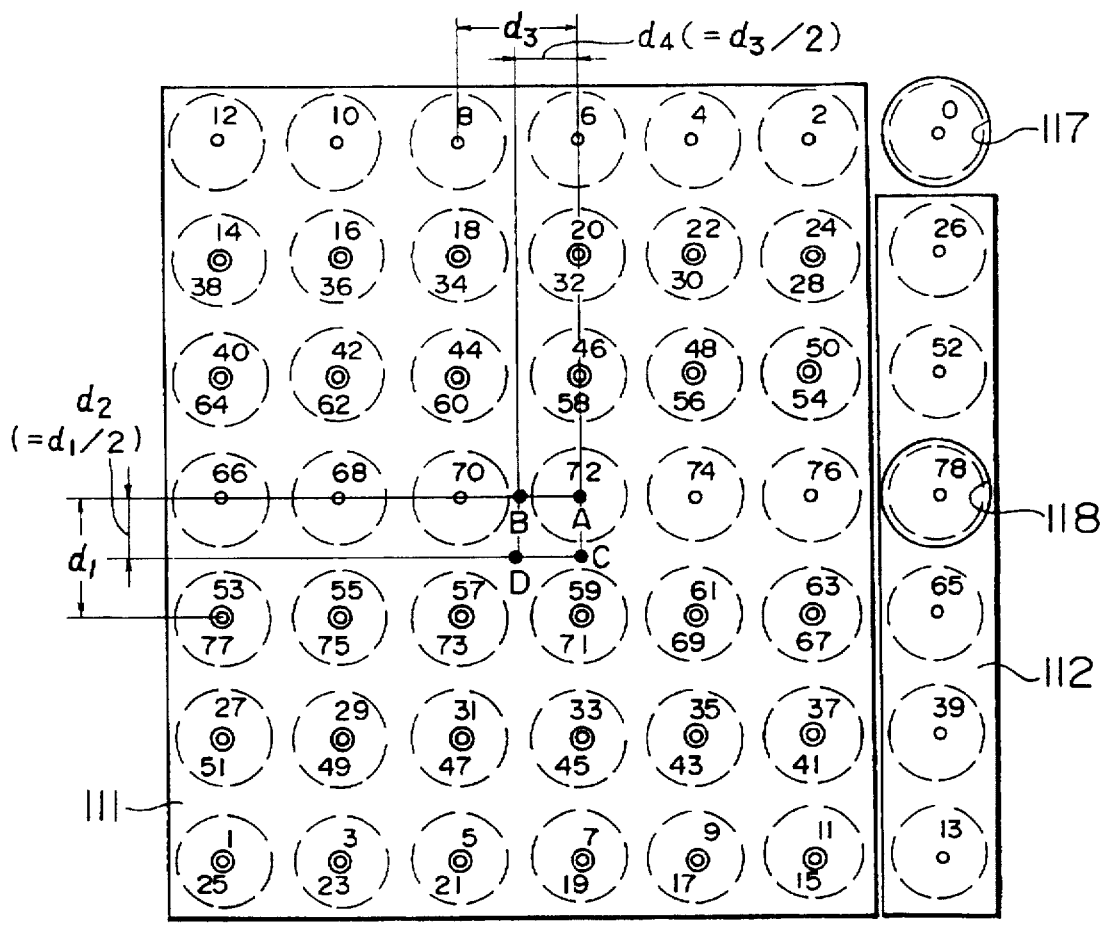
FIG. 7 is an explanatory view showing the image matrix in a method of catching the reflected light emerging from a spot corresponding to the 78th coming and going reflection in which the first embodiment shown in FIG. 4 is used.

FIG. 7 is a view showing an image matrix when the above reflections are repeated a plurality of times, and the light beam is caused to emerge from a spot corresponding to the 78th coming and going reflection. As is clearly understood from this figure, in the first embodiment of the multiple reflection optical instrument of the present invention, the respective centers of curvature A, B, C and D of the four pieces of objective mirrors 113, 114, 115 and 116 focused on the surface of the main field mirror 111 has the following additional definitions in addition to the foregoing definitions (a) to (d). Namely, the vertical distance $d_2$ between the centers of curvature A and C (or B and D) is a half of the distance $d_1$ between two spots vertically adjacent to each other, and the horizontal distance $d_4$ between the centers of curvature A and B (or C and D) is a half of the distance $d_3$ between two spots horizontally adjacent to each other.

Figure 10:
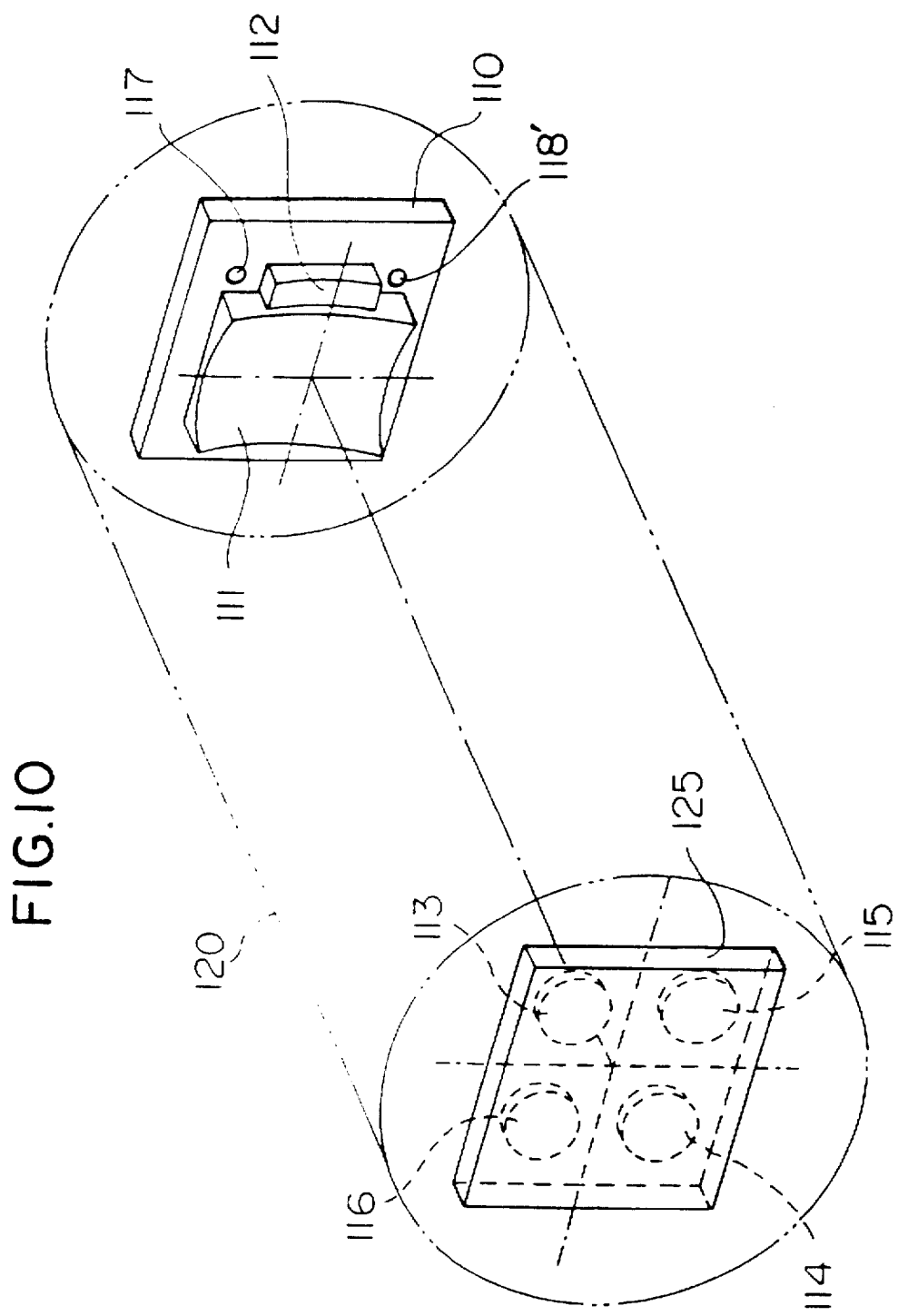
FIG. 10 is a schematic perspective view showing a second embodiment of a multiple reflection optical instrument of the present invention.

A second embodiment of the multiple reflection optical instrument of the present invention is shown in FIG. 10. Since the second embodiment differs from the first one only in that an outlet window 118' is not formed on the auxiliary field mirror 112, but formed on a corner portion of the mount 110 where is lower than a lower edge of the auxiliary field mirror 112, the detailed description thereof is omitted for avoiding repetition.

Figure 11:
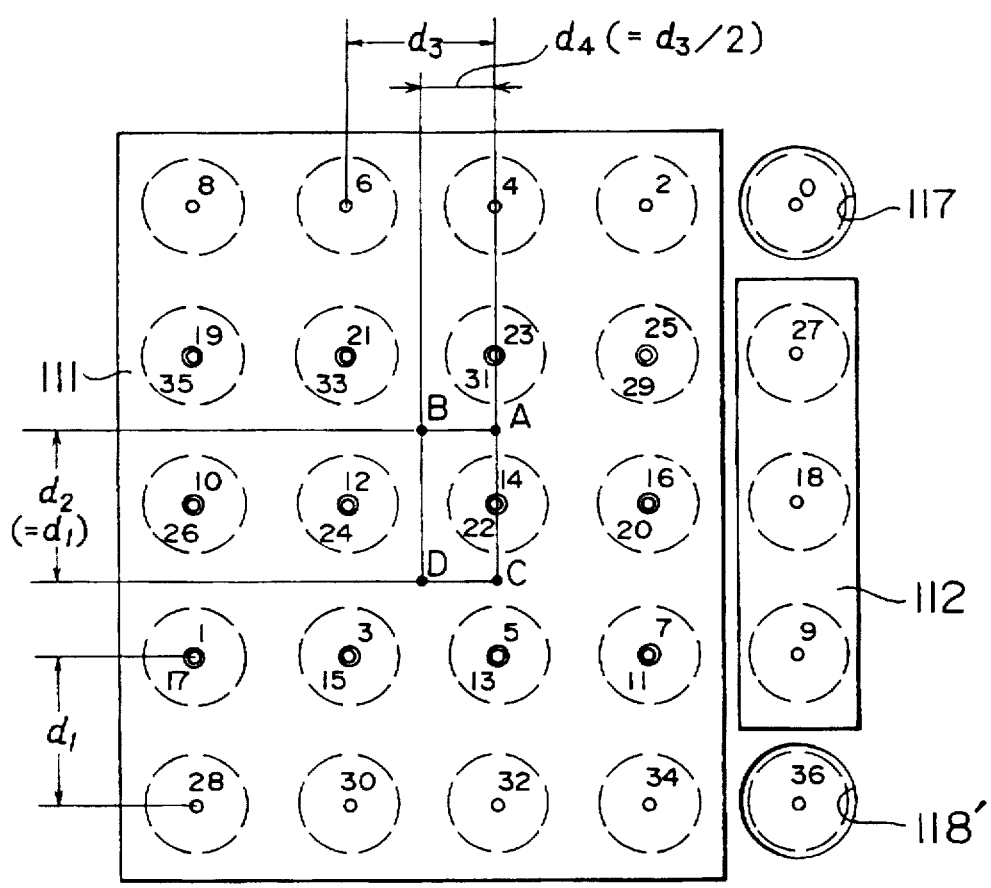
FIG. 11 is an explanatory view showing an image matrix in a method of catching the reflected light using the embodiment shown in FIG. 10.

One exemplified image matrix formed on the main and auxiliary field mirrors 111 and 112 by using the second embodiment is shown in FIG. 11. As is understood from FIG. 11, in a reflected light catching method according to this example, a light beam introduced through an inlet window 117 into a housing is caused to emerge through the outlet window 118' to an outside of the housing as the 36th coming and going reflected light beam.

The arrangement of columns and lines of the image matrix shown in FIG. 11 is determined such that the following conditions are satisfied.

(i) The point A of symmetry between the position 0 of the inlet light beam at the incident window 117 and the first spot 1 focused through the first objective mirror 113 at a cross point of a left end column of the image matrix and a second line from the bottom thereof becomes the center of curvature of the first objective mirror 113.

(ii) The point B of symmetry between the first spot 1 and the second spot 2 focused through the second objective mirror 114 at a cross point of the right end column of the image matrix formed on the main field mirror 111 and the uppermost line thereof becomes the center of curvature of the second objective mirror 114.

(iii) A point C of symmetry between the spot 9 in the lowermost line on the auxiliary field mirror 112 and the spot 10 focused through the third objective mirror 115 at a cross point of the left end column of the image matrix and the third line from the top thereof becomes the center of curvature of the third objective mirror 115.

(iv) A point D of symmetry between the spot 10 and the spot 11 focused through the fourth objective mirror 116 at a cross point of the right end column of the image matrix formed on the main field mirror 111 and the second line from the bottom thereof becomes the center of curvature of the fourth objective mirror 116.

In addition, the vertical distance $d_2$ between the centers A and C (or B and D) is the same as the distance $d_1$ between two spots vertically adjacent to each other, and the horizontal distance $d_4$ between the centers A and B (or C and D) is a half of the distance $d_3$ between two spots horizontally adjacent to each other.

What is claimed is:

1. A reflected light receiving method in a multiple path optical matrix system, including:

causing a light beam from a light source to pass through an inlet window formed at a corner portion of one longitudinal end of a housing provided in a cell and causing the light beam to be incident on a first objective mirror of four pieces of objective mirrors having equal radii of curvature to one another and mechanically mounted on a holder arranged at the other longitudinal end of the housing to be freely rotated about vertical and horizontal axes with respect to an image matrix, reflecting the light beam by the first objective mirror and causing the light beam to be incident on a first spot of a lowermost line in a column on one end side of the image matrix formed on a main field mirror having the same radius of curvature as that of the objective mirrors and arranged on one longitudinal end of the housing such that a center of curvature matches a center of symmetry of the four pieces of objective mirrors along a longitudinal axis of the housing, directing the light beam reflected from the first spot on the main field mirror to a second objective mirror placed at a diagonal position with respect to the first objective mirror, directing the light beam reflected from the second objective mirror to the main field mirror, then reflecting the light beam thereby to the first objective mirror, alternately repeating a reflection between the first objective mirror and the main field mirror and a reflection between the second objective mirror and the main field mirror a plurality of times, and causing the light beam to reach the column vertically focused on one side of the image matrix which includes the first spot, causing the reflected light beam present on the spot at one side to be incident, through the first objective mirror, an auxiliary field mirror arranged adjacent to the main field mirror on the inlet window side, and having the same curvature as that of the objective mirrors and a center of curvature matching a point of symmetry between the first and third objective mirrors, subsequently reflecting the light beam by the auxiliary field mirror to the third objective mirror arranged at a position parallel to the second objective mirror and perpendicular to the first objective mirror, causing the light beam from the third objective mirror to be incident on the main field mirror again and then reflecting the light beam thereby to a fourth objective mirror placed at a diagonal position with respect to the third objective mirror, directing the light beam reflected by the fourth objective mirror to the main field mirror, then reflecting the light beam thereby to the third objective mirror, and alternately repeating a reflection between the third objective mirror and the main field mirror and a reflection between the fourth objective mirror and the main field mirror a plurality of times, alternately repeating the reflections between the first and second objective mirrors and the main field mirror a plurality of times again, alternately repeating the reflections between the third and fourth objective mirrors and the main field mirror a plurality of times again, and causing the light beam finally passing through the housing to emerge from the housing through an outlet window formed on one longitudinal side of and one end of the housing, wherein the finally passing light beam is a reflected light beam toward a spot corresponding to a maximum even-numbered coming and going reflection in the image matrix, the reflected light beam toward the spot corresponding to the even-numbered coming and going reflection is a light beam finally reflected through the third objective mirror, and the finally reflected light beam is caused to emerge from the housing through the outlet window formed at a cross point of the other end side of the image matrix including spots focused on the auxiliary field mirror and the center line thereof.

2. A reflected light receiving method in a multiple path optical matrix system, including:

causing a light beam from a light source to pass through an inlet window formed at a corner portion of a mount arranged at one longitudinal end of a housing provided in a cell and causing the light beam to be incident on a first objective mirror of four pieces of objective mirrors having equal radii of curvature to one another and mechanically mounted on a holder arranged at the other longitudinal end of the housing to be freely rotated about vertical and horizontal axes with respect to an image matrix, reflecting the light beam by the first objective mirror and causing the light beam to be incident on a first spot of the image matrix formed on a main field mirror having the same radius of curvature as that of each of the objective mirrors and arranged on one longitudinal end of the housing such that a center of curvature matches a center of symmetry of the four pieces of objective mirrors along a longitudinal axis of the housing, directing the light beam reflected from the first spot on the main field mirror to a second objective mirror placed at a diagonal position with respect to the first objective mirror, directing the light beam reflected from the second objective mirror to the main field mirror, then reflecting the light beam thereby to the first objective mirror, alternately repeating a reflection between the first objective mirror and the main field mirror and a reflection between the second objective mirror and the main field mirror a plurality of times, and causing the light beam to reach the column vertically focused on one end side of the image matrix which includes the first spot, causing the reflected light beam present on the spot at one end side to be incident, through the first objective mirror, on an auxiliary field mirror arranged adjacent to the main field mirror on the inlet window side, and having the same curvature as that of each of the objective mirrors and a center of curvature matching a point of symmetry between the first and third objective mirrors, subsequently reflecting the light beam by the auxiliary field mirror to the third objective mirror arranged at a position parallel to the second objective mirror and perpendicular to the first objective mirror, causing the light beam from the third objective mirror to be incident on the main field mirror again and then reflecting the light beam thereby to a fourth objective mirror placed at a diagonal position with respect to the third objective mirror, directing the light beam reflected by the fourth objective mirror to the main field mirror, then reflecting the light beam thereby to the third objective mirror, and alternately repeating a reflection between the third objective mirror and the main field mirror and a reflection between the fourth objective mirror and the main field mirror a plurality of times, alternately repeating the reflections between the first and second objective mirrors and the main field mirror a plurality of times again, alternately repeating the reflections between the third and fourth objective mirrors and the main field mirror a plurality of times again, and causing the light beam finally passing through the housing to emerge from the housing through an outlet window formed on one longitudinal side of and one end of the housing, wherein said first spot is focused at a cross point of one end column of the image matrix on the main field mirror where is spaced most apart from the auxiliary field mirror and a second line from the bottom thereof and, on the other hand, the finally passing light beam is a reflected light beam directed to a spot corresponding to a maximum even-numbered coming and going reflection in the image matrix, the reflected light beam toward the spot corresponding to the even-numbered coming and going reflection is a light beam finally reflected through the third objective mirror, and the finally reflected light beam is caused to emerge from the housing through the outlet window formed at a cross point of the other end column of the image matrix including spots focused on the auxiliary field mirror and in the lowermost line thereof.

3. A reflected light catching method as claimed in claim 1, wherein a position of a center of curvature of each of the four pieces of objective mirrors, which is projected onto the main field mirror, is adjusted such that a number of lines of spots arranged in a horizontal direction of the image matrix are an odd number.

4. A reflected light catching method as claimed in claim 2, wherein a position of a center of curvature of each of the four pieces of objective mirrors, which is projected onto the main field mirror, is adjusted such that a number of lines of spots arranged in a horizontal direction of the image matrix are an odd number.

* * * * *

UNITED STATES PATENT AND TRADEMARK OFFICE
CERTIFICATE OF CORRECTION

PATENT NO.: 5,798,880

DATED: August 25, 1998

INVENTOR(S): Yamamoto

It is certified that error appears in the above-identified patent and that said Letters Patent is hereby corrected as shown below:

Col. 1, ln. 54 reads "light beam beam finally" and should read --light beam finally--

Col. 2, ln. 28 reads "and is catched" and should read --and is caught--

Col. 7, ln. 34 reads "can be certainly catched" and should read --can be certainly caught--

Col. 11, ln. 67 reads "reflected light beam gotten out from" and should read --reflected light beam retrieved from--

Signed and Sealed this

First Day of December, 1998

Attest:

BRUCE LEHMAN

Attesting Officer

Commissioner of Patents and Trademarks